United States Patent [19]

Heebner et al.

[11] 4,441,124
[45] Apr. 3, 1984

[54] TECHNIQUE FOR INSPECTING SEMICONDUCTOR WAFERS FOR PARTICULATE CONTAMINATION

[75] Inventors: Richard W. Heebner, Solebury Township, Bucks County, Pa.; Randal L. Schmitt, Plainsboro Township, Middlesex County, N.J.

[73] Assignee: Western Electric Company, Inc., New York, N.Y.

[21] Appl. No.: 318,523

[22] Filed: Nov. 5, 1981

[51] Int. Cl.³ .............................................. H04N 7/18
[52] U.S. Cl. ................................... 358/106; 250/574; 356/237
[58] Field of Search ................ 358/106; 356/335, 336, 356/337, 338, 339, 340, 343, 237; 250/563, 572, 574

[56] References Cited

U.S. PATENT DOCUMENTS

| | | | |
|---|---|---|---|
| 3,589,813 | 6/1971 | Sturzinger | 356/72 |
| 3,624,835 | 11/1971 | Wyatt | 250/574 |
| 3,767,306 | 10/1973 | Mast et al. | 356/102 |
| 3,807,868 | 4/1974 | Simila | 356/237 |
| 4,084,902 | 4/1978 | Green | 356/38 |
| 4,197,011 | 4/1980 | Hudson | 356/237 |
| 4,208,126 | 6/1980 | Cheo et al. | 356/51 |
| 4,286,293 | 8/1981 | Jablonski | 358/199 |

OTHER PUBLICATIONS

Grosewald et al.-Automatic Detection of Defects on Wafers-IBM Tech. Bull., vol. 21, #6, Nov. 1978, pp. 2336-2337.
Hopkins-Optical Scanner for Surface Analysis—IBM Tech. Bull., vol. 20, #11B, Apr. 1978-pp. 4939-4940.
Tech. Note-Automatic Inspection of Silicon Wafers-Optics and Laser Technology-Dec. 1980, pp. 317-320.
Scanning Laser Senses Wafer Defects-Electronics--Mar. 16, 1978, pp. 48, 50.

Primary Examiner—Joseph A. Orsino, Jr.
Attorney, Agent, or Firm—D. J. Kirk

[57] ABSTRACT

A laser beam (88) is raster scanned over the surface of a patterned semiconductor wafer (66) at an angle normal thereto. A plurality of detectors, radially spaced from the wafer (66) and substantially coplanar therewith detect light scattered from contaminating particulate thereon. The detected light is converted into a video signal that is forwarded to a video monitor (84) to display the particulate material while eliminating the patterned surface background.

6 Claims, 4 Drawing Figures

TECHNIQUE FOR INSPECTING SEMICONDUCTOR WAFERS FOR PARTICULATE CONTAMINATION

TECHNICAL FIELD

The instant invention is directed to a technique for inspecting semiconductor wafers. In particular, such wafers are inspected for particulate contamination thereon.

BACKGROUND OF THE INVENTION

In-process inspection of semiconductor wafer surfaces is playing an ever increasing role in the fabrication of integrated circuits. With shrinking surface dimensions and the increasing number of components per chip, various inspection techniques are now used to monitor for defects and contaminants on the surface of semiconductor wafers during production in an effort to increase yields. Since the features on the wafers are on the order of microns, even very small particulates (e.g., dust, silicon chips, photoresist flakes, etc.) can ruin an otherwise acceptable device. Determination of the presence and location of any contaminants on the wafer surface can (1) aid in locating the source of the contamination in order to prevent future contamination, and (2) assist in determining whether or not to discard a particular wafer due to excessive contamination that can lead to the failure of many or most of the devices on the wafer.

Small particles are difficult to see when various circuit patterns are present on the wafer. An operator must scrutinize the inspected area in detail to determine defects from the patterned background of the wafer surface. Such a technique is tedious and time consuming resulting in operator fatigue and errors. Additionally, inspections are presently carried out manually by operators viewing the wafers using standard reflection mode optical microscopes. Although such manual techniques work well, they are time consuming and only a small number of circuit areas on a limited number of wafers can be inspected. For statistical purposes such sampling is too small.

Accordingly, there is a need for a wafer inspection technique that can readily discriminate between the contaminating particulate and the features or patterns on the wafer surface. Additionally, such a technique should be able to detect the particulates contaminating the surface of a wafer while automatically recording, the real-time, the position and size of the particulate.

SUMMARY OF THE INVENTION

The instant invention overcomes the foregoing problems with a method for detecting particulate material on the surface of a patterned wafer. The method comprises the steps of scanning a beam of light over the surface of the wafer at an angle normal thereto; and monitoring light scattered at such an angle as to detect only the light scattered from the particulate.

Furthermore, the detected light scattered from the particulate material is converted into a video signal representation of the particulate which is used to modulate a scanning electron beam of a video monitor to form an image of the particulate on a screen of the video monitor.

DETAILED DESCRIPTION

Figure 1:
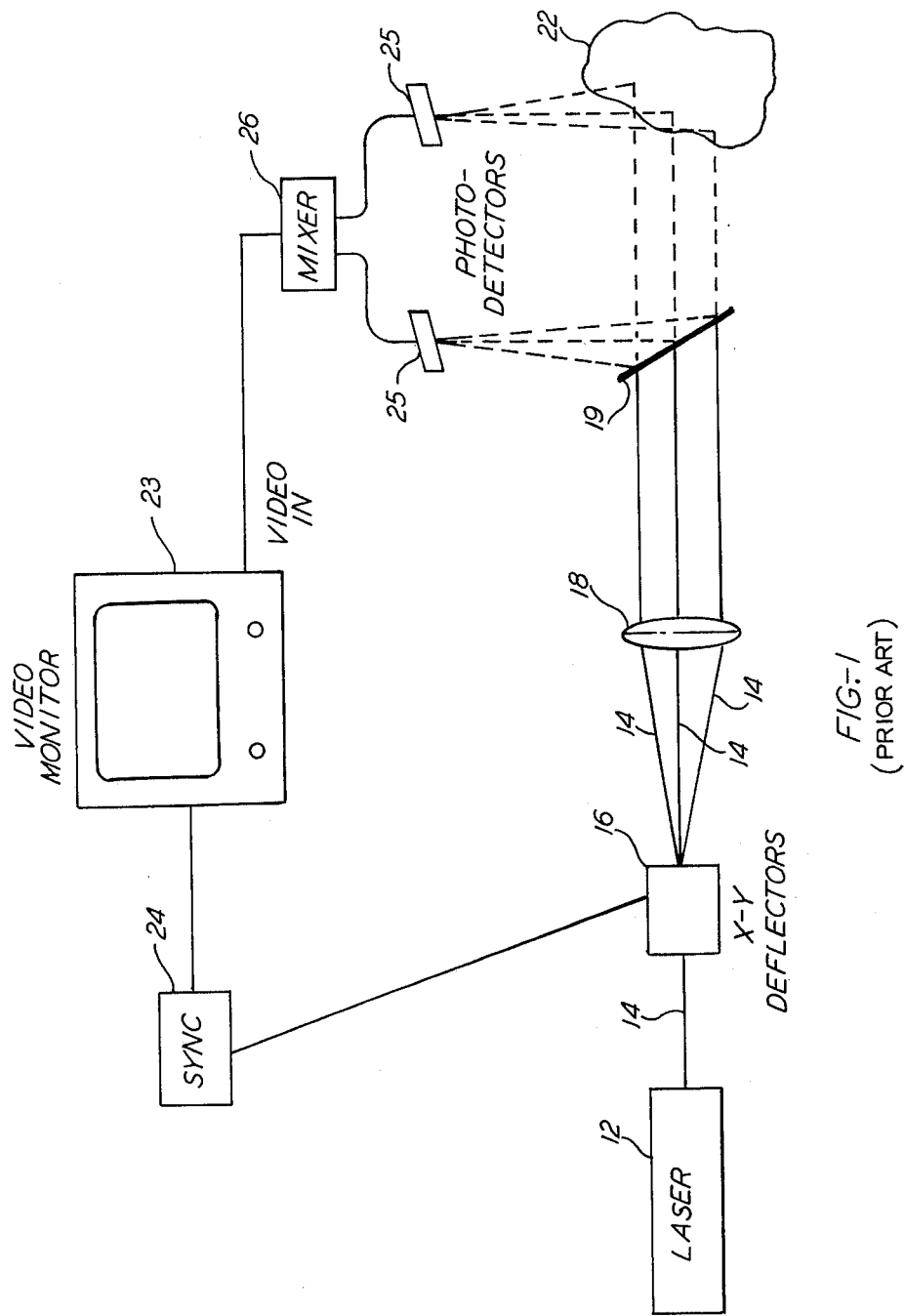
FIG. 1 is a schematic diagram of a prior art object scanning technique.

The operating principles of the present invention are based on an object scanning technique set forth in U.S. Pat. No. 4,286,293, which issued on Aug. 25, 1981 to Jablonowski, assigned to the instant assignee, which is incorporated herein by reference. The object scanning technique, illustrated in FIG. 1, employs a laser 12 to direct a narrow light beam 14 towards X-Y deflectors 16 which raster scan the beam 14 through a focusing lens 18 and a beamsplitter 19 to provide localized illumination on the surface of an object 22. Additionally, the scanning rate of the X-Y deflectors 16 is synchronized with the scanning beam rate of a video monitor 23 via a sync circuit 24. A plurality of remote photodetectors 25-25 monitor the light scattered from the laser scanned object 22 and the output of the detectors pass through a mixer 26 to modulate the intensity of a scanning electron beam of the video monitor 23 to produce an image of the object. Accordingly, the object scanning technique converts two-dimensional spatial information into a one-dimensional electrical signal (the video signal) and the video monitor 23 simply transforms the one-dimensional video signal back into a two-dimensional image.

Image contrast enhancement is achieved by not only monitoring the intensity of light scattered from the object 22, but may be further enhanced by monitoring polarization, scattering angle variations, fluorescence or other variables as described in the Jablonowski patent. In addition, multiple detectors 25-25 can provide multiple video images which can be combined through addition and/or subtraction to obtain a video image of optimum contrast.

Figure 2:
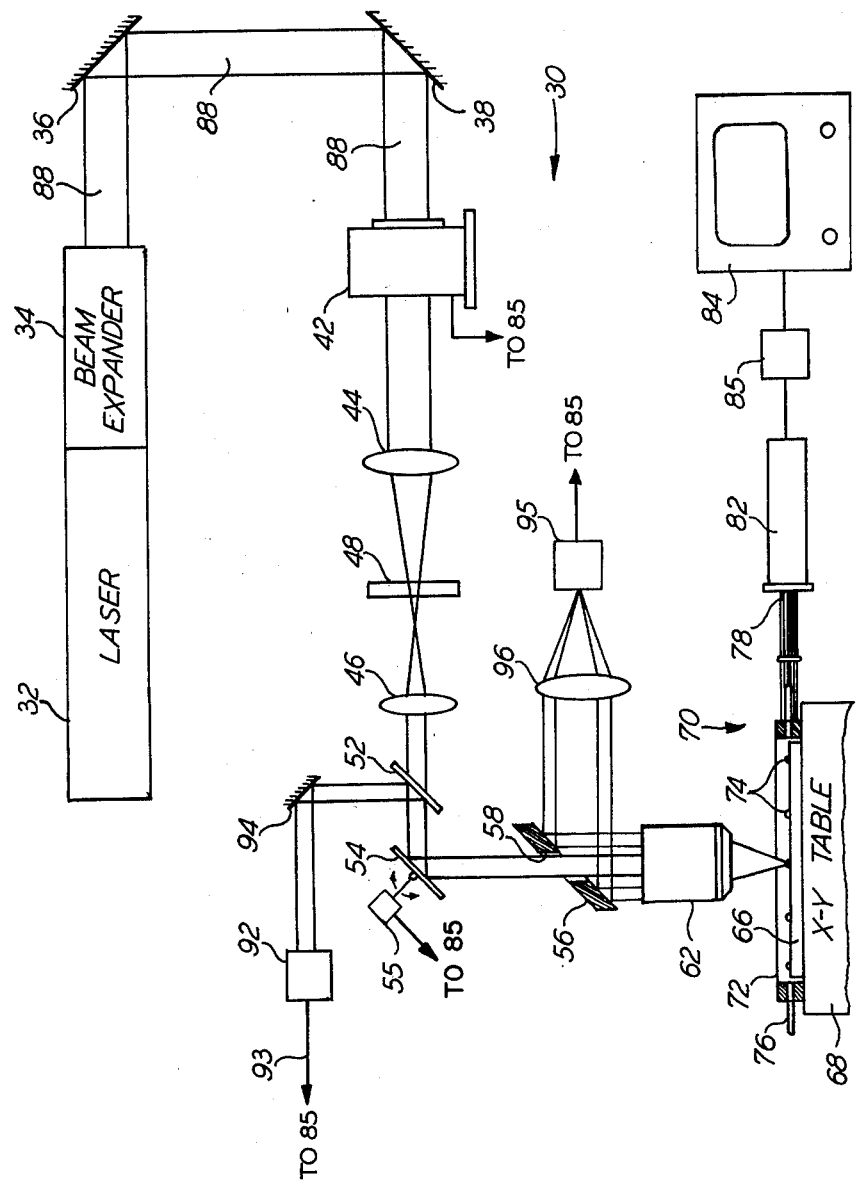
FIG. 2 is a schematic drawing of an optical scanning system incorporating the instant inventive concepts.

The instant exemplary optical system, generally referred to by the numeral 30, is shown schematically in FIG. 2. The system 30 is comprised of a laser 32 (e.g., HeNe), a beam expander 34, first and second fixed mirrors 36 and 38, respectively, an acousto-optic deflector 42, first and second focusing lenses 44 and 46, respectively, a cylindrical lens 48, a beamsplitter 52, a rotatable mirror 54 controlled by a galvanometer 55, an annular mirror 56 having a central aperture 58 and a microscope objective 62.

Figure 3:
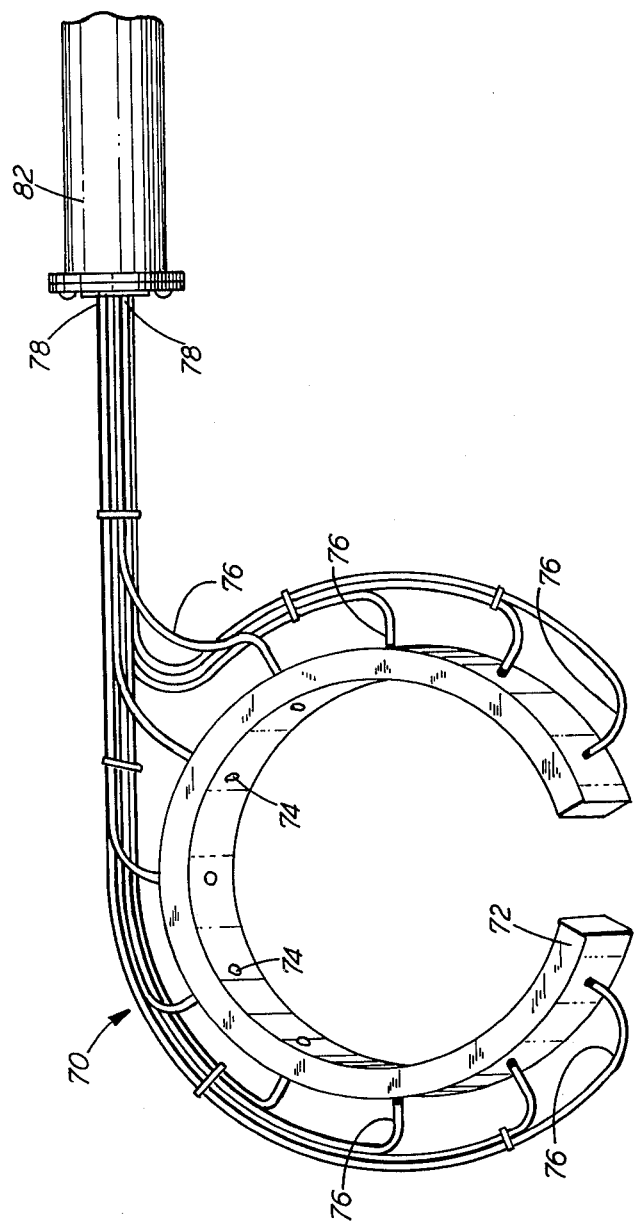
FIG. 3 is an isometric drawing of a light detection apparatus used to implement the instant invention.

A semiconductor wafer 66 is shown positioned on an X-Y table 68 located under the microscope objective 62. A light detector system 70, shown in detail in FIG. 3, is spaced from and surrounds the wafer 66. The detector system 70 is comprised of a ring 72 which receives a plurality of first ends 74-74 of optical fiber cables 76-76. Second ends 78-78 of the cables 76-76 terminate in a photo-mutliplier tube detector 82 (also see FIG. 2). The output of the detector 82 is connected to a video monitor 84 via a combined sync-mixer circuit 85. The sync-mixer circuit 85 provides synchronization signals between the video monitor 84 and the galvanometer 55 and the acousto-optic deflector 42. Additionally, the circuit 85 can select and/or combine video signals input thereto.

In operation (see FIG. 2), a wafer 66 is placed on the X-Y table 68 inside the holder 72 with the first ends 74-74 of the optical fiber cables 76-76 being substantially in coplanar relation to the wafer and radially directed thereat. The wafer 66 used in an exemplary embodiment was made of silicon having a diameter of 100 mm and approximately 5 mils thick. The laser 32 is activated and the output therefrom increased in diameter by the expander 34 as beam 88 which is reflected by the mirrors 36 and 38 into the acousto-optic deflector 42 which scans the beam 88 in a first direction at the same rate and in synchronization with the horizontal line scan of the video monitor 84 (e.g., 53.5 μs constant velocity scan followed by a 10 μs flyback period).

The scanned laser beam 88 passes through the lenses 44, 48 and 46 and the beamsplitter 52 and impinges on the rotatable mirror 54. The lenses 44 and 46 form a 2:1 telecentric lens system while the cylindrical lens 48 compensates for astigmatism introduced by the acousto-optic deflector 42. The mirror 54 oscillates at 60 Hz under control of the galvanometer 55 to provide a scan rate in synchronization with the vertical scan rate of the video monitor 84. The laser beam 88, now scanned in two orthogonal directions, passes through the opening 58 in the annular mirror 56 and then passes through the flat field microscope objective 62 which focuses the beam on the surface of the wafer 66 and executes a raster scan thereon.

Light that is reflected or scattered at low angles (i.e., substantially normal to the surface of the wafer) from the wafer 66 is collected by the objective 62 and collimated. Some of this radiation passes through the aperture 58 in the annular mirror 56 and is directed to a bright field PIN detector 92, via the beamsplitter 52 and an auxiliary mirror 94, which has an output 93 connected to the sync-mixer circuit 85. The output of the detector 92 provides video image information which is substantially the same as the information required to form a bright field microscope image.

The remainder of the scattered light collected by the microscope objective 62 is intercepted by the lower, reflective, surface of the annular mirror 56 and directed to a dark field PIN detector 95 via a lens 96. The video output from the detector 95 contains higher spatial frequency information and substantially corresponds to a dark field microscope image. The video output of the detector 95 is also electrically connected to the sync-mixer circuit 85.

Much of the light from the normally scanned beam 88 is scattered from the wafer 66 will not be collected by the microscope objective 62 due to its limited numerical aperture. This is particularly true if the wafer 66 has a pattern with sharp edges or small features. However, a patterned wafer 66 having no particulate material thereon will scatter substantially no light along the wafer surface, while a wafer having particulate thereon will scatter a portion of the light impinging thereon along the surface. The instant apparatus 30 utilizes such high angle light scattering (i.e., substantially along the wafer surface) to great advantage to form an image of any particles contaminating the surface of the patterned wafer 66 without imaging the pattern itself. This technique not only frees the operator from picking out particulates from a complex background pattern but it also lends itself to simple and efficient techniques for data processing in an automated system.

Accordingly, in the instant apparatus 30 the detector 82 is positioned so as to maximize the ratio of the scattered light from the particles to the diffracted light from the pattern. A narrow passband filter in the PMT detector 82 rejects light other than that at the laser wavelength which is 632.8 mm in the exemplary embodiment. The ring 72, with the fiber bundle ends 74-74 extending therethrough, which surrounds the wafer 66, is placed at a relatively low angle which is substantially parallel to the patterned surface of the wafer 66, so that the more intense low order diffracted light will be eliminated from the field of view.

In practice, the ring 72 may be initially positioned about the wafer 66 and in coplanar relation thereto. The ring 72 may then be moved upward (i.e., away from the wafer 66) until portions of the wafer pattern appears on the monitor 84. The ring 72 is then moved towards the wafer 66 until the pattern no longer appears on the monitor 84. The optimum angle of the ring 72 to the wafer 66 will depend on the depth of the pattern on the wafer surface.

The laser scanning rate of the apparatus 30 is synchronized with the electron beam scanning of the video monitor 84 and the outputs of the detectors 82, 92 and 95 are used to selectively modulate the intensity of the video monitor 84 in a well known fashion. If only the video output of the bright field detector 92 is used a bright field image will be shown on the screen of the video monitor 84 and when only the video output of the detector 95 is used a dark field image will be obtained. The video outputs from the detectors 92 and 95 may be combined (e.g., subtracted) to form an enhanced composite video signal as described in the aforementioned Jablonowski patent.

Additionally, when the ring 72 is positioned in substantially coplanar relation to the surface of the wafer 66, as hereinbefore described, only the light scattered by particulate on that surface is transmitted through the fiber cables 76-76 to the detector 82 to form an image on the screen of the video monitor 84. Thus, an operator can view the screen to readily determine the location of particulate on the wafer surface by imaging only the particulate. Also the particulate and the surface pattern may be simultaneously shown by showing the bright field or the dark field on the screen of the video monitor 82 while superimposing the video signal from the particulate detector 82 thereon.

In an exemplary embodiment the microscope objective 62 was a Leitz C108204, 8× power having a numerical aperture of 0.18 which resulted in a field size of approximately 350 μm by 260 μm at a working distance of approximately 13.9 mm. Accordingly, after scanning the first field, the X-Y table 68 is indexed to a second field which is scanned as hereinbefore described. Such indexing is repeated until the full surface of the wafer 66 has been scanned.

Figure 4:
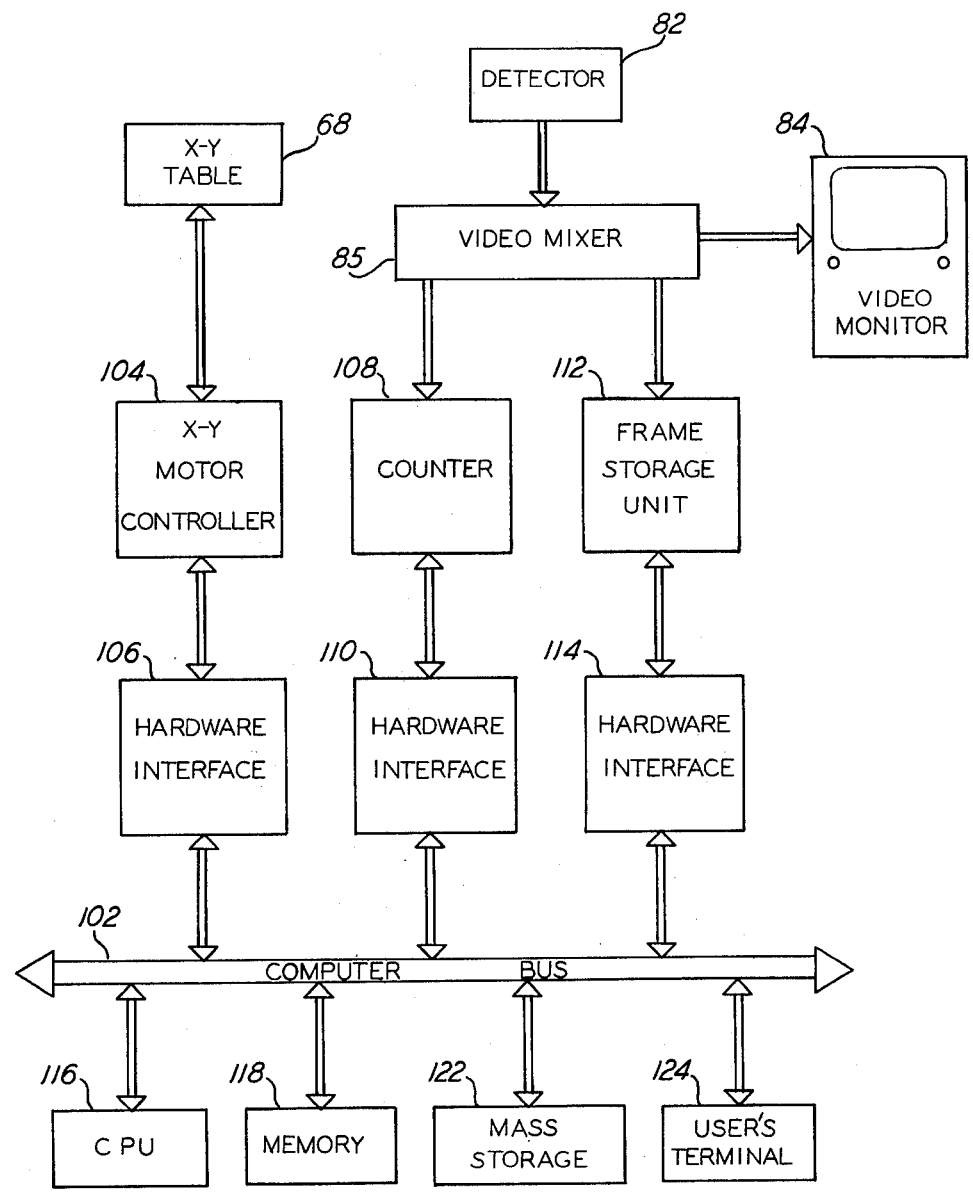
FIG. 4 is a block diagram of an automated system incorporating the instant concepts.

FIG. 4 is a block diagram of an exemplary automated system for determining the size and location of particulates on the surface of a semiconductor wafer. The X-Y table 68, the detector 82, video monitor 84 and the sync-mixer circuit 85 function as hereinbefore set forth as described in relation to FIG. 2. The X-Y table 68 is electrically connected to a computer bus 102 via an X-Y table controller 104 and hardware interface apparatus 106 while the video sync-mixer circuit 85 is also electrically connected to the bus 102 via a counter 108 and hardware interface apparatus 110 in parallel with a frame storage unit 112 and hardware interface apparatus 114. A Central Processing Unit (CPU) 116, a memory apparatus 118, mass storage apparatus and a user's terminal 124 are also connected in parallel to the computer bus 102.

In operation, under computer program control, the X-Y table 68 is positioned to a predetermined location to present a first field-of-view of the surface of the wafer 66 to the scanning apparatus 30. The laser beam 88 (see FIG. 2) scans the first field of view as hereinbefore set forth. The video signal representing detected particulate on the surface of the wafer 66 is transmitted from the sync-mixer circuit 85 to the counter 108. Upon completion of one full video frame, the CPU 116 reads the total count of the number of "particle encounters" during the frame. If the count is above some predetermined acceptable level the CPU 116 will instruct the video frame mass storage unit 112 to store the frame information. After the storage of the frame information the CPU 116 will direct the transfer of the information from the frame storage unit 112 to the computer memory 118 for analysis. The CPU 116 can determine both the size and location of the particles within the frame using well known algorithms. Such size and location information is then placed in the mass storage 122, on disk, magnetic tape or the like, for future reference or to generate a map of particulate on a specific field or the entire wafer 66. The CPU 116 then instructs the X-Y motor controller 104 to move the X-Y table 68 to a second field-of-view on the surface of the wafer 66 and repeat the foregoing steps. This procedure is automatically repeated until the entire surface of the wafer 66 has been scanned.

Based upon the instant inspection technique the computer can store various information such as (1) total number of particles, (2) average particle size, (3) size distribution; (4) spatial distribution of particles, and (5) particles located in "critical areas" of the wafer or other information of interest. This information can be displayed at the user's terminal 124 on a CRT or printed out on off-line equipment (not shown).

It is to be understood that the embodiments described herein are merely illustrative of the principles of the invention. Various modifications may be made thereto by persons skilled in the art which will embody the principles of the invention and fall within the spirit and scope thereof.

What is claimed is:

1. An apparatus for detecting particulate material on the surface of a semiconductor wafer having a pattern thereon, comprising:
   means for scanning a beam of light over the patterned surface of the wafer at an angle normal thereto; and
   a plurality of detectors mounted circumferential of the wafer and substantially coplanar with the surface thereof for detecting light scattered substantially along the surface of the wafer by the particulate material and not the pattern.

2. The apparatus as set forth in claim 1 comprising:
   means for converting the monitored light into a first video signal representation of the particulate.

3. The apparatus as set forth in claim 2, comprising:
   means for modulating a scanning electron beam of a video monitor with said first video signal to form an image of the particulate on said monitor.

4. The apparatus as set forth in claim 2, comprising:
   means for forwarding the video signal representation to a computer to determine the size and location and quantity of particulate on the wafer surface.

5. The apparatus as set forth in claim 4, comprising:
   means for monitoring light scattered from the surface of the wafer in a direction substantially normal thereto which is indicative of at least the wafer pattern; and
   means for converting the monitored light into a second video signal representing the wafer pattern.

6. The apparatus as set forth in claim 5, comprising:
   means for further modulating the scanning electron beam of the video monitor with the second video signal to simultaneously form an image of the pattern and particulate on said monitor.

* * * * *